United States Patent
Reyhan et al.

(10) Patent No.: US 8,960,422 B2
(45) Date of Patent: *Feb. 24, 2015

(54) PACKAGED ANTIMICROBIAL MEDICAL DEVICE AND METHOD OF PREPARING SAME

(71) Applicant: Ethicon, Inc., Somerville, NJ (US)

(72) Inventors: Mehmet Reyhan, East Windsor, NJ (US); Robert Cerwin, Pipersville, NJ (US)

(73) Assignee: Ethicon, Inc., Somverville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/801,819

(22) Filed: Mar. 13, 2013

(65) Prior Publication Data
US 2013/0193008 A1      Aug. 1, 2013

Related U.S. Application Data

(60) Division of application No. 12/415,600, filed on Mar. 31, 2009, which is a continuation-in-part of application No. 11/301,365, filed on Dec. 13, 2005, now Pat. No. 7,513,093, which is a
(Continued)

(51) Int. Cl.
*A61B 17/04*      (2006.01)
*A61B 17/06*      (2006.01)
(Continued)

(52) U.S. Cl.
CPC ............ *A61B 17/04* (2013.01); *A61B 17/06114* (2013.01); *A61B 17/06166* (2013.01); *A61B 19/02* (2013.01); *A61L 17/005* (2013.01); *A61B 2019/0274* (2013.01)
USPC ......................................... 206/63.3; 206/210

(58) Field of Classification Search
USPC ........ 206/63.3, 380, 480, 363, 438, 205, 207, 206/210
See application file for complete search history.

(56) References Cited

U.S. PATENT DOCUMENTS

| 809,725 A | 1/1906 | Neff |
| 2,917,878 A | 12/1958 | Carnaruis et al. |

(Continued)

FOREIGN PATENT DOCUMENTS

| AU | 52834/86 B | 2/1987 |
| CA | 2185056 A1 | 3/1997 |

(Continued)

OTHER PUBLICATIONS

U.S. Appl. No. 60/416,114, filed Oct. 4, 2002.
(Continued)

*Primary Examiner* — Steven A. Reynolds
(74) *Attorney, Agent, or Firm* — Roberts Mlotkowski Safran & Cole, P.C.

(57) ABSTRACT

A method of making a packaged antimicrobial suture. The method includes the steps of providing a containment compartment molded from a polymeric resin comprising a polymeric material and an antimicrobial agent, positioning a suture within the containment compartment, the suture comprising one or more surfaces; covering the containment compartment having the suture in an outer package cover having an inner surface, and subjecting the outer package, the containment compartment and the suture to time, temperature and pressure conditions sufficient to vapor transfer an effective amount of the antimicrobial agent from the containment compartment to the suture, while retaining an effective amount of the antimicrobial agent on the containment compartment, thereby substantially inhibiting bacterial colonization on the suture and the containment compartment. A packaged antimicrobial suture is also provided.

7 Claims, 6 Drawing Sheets

Related U.S. Application Data continuation-in-part of application No. 11/301,364, filed on Dec. 13, 2005, now Pat. No. 8,133,437, which is a continuation-in-part of application No. 10/808,669, filed on Mar. 25, 2004, now abandoned, which is a continuation-in-part of application No. 10/603,317, filed on Jun. 25, 2003, now abandoned, which is a continuation-in-part of application No. 10/367,497, filed on Feb. 15, 2003, now abandoned.

(60) Provisional application No. 60/416,114, filed on Oct. 4, 2002.

(51) Int. Cl.
*A61B 19/02* (2006.01)
*A61L 17/00* (2006.01)

(56) References Cited

U.S. PATENT DOCUMENTS

| | | | |
|---|---|---|---|
| 2,947,282 A | 8/1960 | Brown | |
| 3,068,864 A | 12/1962 | Tietze | |
| 3,202,273 A | 8/1965 | Riall | |
| 3,613,879 A * | 10/1971 | Kemble | 206/210 |
| 3,629,477 A | 12/1971 | Model et al. | |
| 3,642,003 A | 2/1972 | Kurtz | |
| 3,726,057 A | 4/1973 | Kemble | |
| 3,767,362 A | 10/1973 | Griffin et al. | |
| 3,815,315 A | 6/1974 | Glick | |
| 3,839,297 A | 10/1974 | Wasserman et al. | |
| 3,862,304 A | 1/1975 | Kurtz | |
| 3,896,812 A | 7/1975 | Kurtz | |
| 3,939,971 A | 2/1976 | Tulis | |
| 3,991,766 A | 11/1976 | Schmitt et al. | |
| 4,024,871 A | 5/1977 | Stephenson | |
| 4,027,676 A | 6/1977 | Mattei | |
| 4,105,034 A | 8/1978 | Shalaby et al. | |
| 4,120,395 A | 10/1978 | Mandel et al. | |
| 4,126,221 A | 11/1978 | Cerwin | |
| 4,185,637 A | 1/1980 | Mattei | |
| 4,201,216 A | 5/1980 | Mattei | |
| 4,230,663 A | 10/1980 | Forstrom et al. | |
| 4,476,590 A | 10/1984 | Scales et al. | |
| 4,482,053 A * | 11/1984 | Alpern et al. | 206/439 |
| 4,603,538 A | 8/1986 | Shave | |
| 4,605,564 A | 8/1986 | Kulla et al. | |
| 4,615,705 A | 10/1986 | Scales et al. | |
| 4,728,323 A | 3/1988 | Matson | |
| 4,846,844 A | 7/1989 | De Leon et al. | |
| 4,853,978 A | 8/1989 | Stockum | |
| 4,856,504 A | 8/1989 | Yamamoto et al. | |
| 4,946,043 A | 8/1990 | Roshdy et al. | |
| 4,952,419 A | 8/1990 | De Leon et al. | |
| 4,967,902 A | 11/1990 | Sobel et al. | |
| 5,019,096 A | 5/1991 | Fox, Jr. et al. | |
| 5,037,429 A | 8/1991 | Hermes et al. | |
| 5,052,551 A * | 10/1991 | Cerwin et al. | 206/63.3 |
| 5,066,328 A | 11/1991 | Zlotnik | |
| 5,091,442 A | 2/1992 | Milner | |
| 5,128,101 A | 7/1992 | Boynton | |
| 5,131,534 A * | 7/1992 | Brown et al. | 206/63.3 |
| 5,154,283 A | 10/1992 | Brown | |
| 5,165,913 A | 11/1992 | Hill et al. | |
| 5,180,605 A | 1/1993 | Milner | |
| 5,213,210 A | 5/1993 | Cascio et al. | |
| 5,222,978 A * | 6/1993 | Kaplan et al. | 606/228 |
| 5,230,424 A | 7/1993 | Alpern et al. | |
| 5,261,421 A | 11/1993 | Milner | |
| 5,284,240 A * | 2/1994 | Alpern et al. | 206/63.3 |
| 5,295,979 A | 3/1994 | DeLaurentis et al. | |
| 5,359,831 A | 11/1994 | Brown et al. | |
| 5,366,081 A | 11/1994 | Kaplan et al. | |
| 5,464,580 A | 11/1995 | Popescu et al. | |
| 5,468,252 A | 11/1995 | Kaplan et al. | |
| 5,468,562 A | 11/1995 | Farivar et al. | |
| 5,474,797 A | 12/1995 | Sioshansi et al. | |
| 5,518,730 A | 5/1996 | Fuisz | |
| 5,529,175 A | 6/1996 | Brunken | |
| 5,534,288 A | 7/1996 | Gruskin et al. | |
| 5,555,976 A | 9/1996 | Pernot | |
| 5,556,699 A | 9/1996 | Niira et al. | |
| 5,562,211 A | 10/1996 | Simons et al. | |
| 5,607,681 A | 3/1997 | Galley et al. | |
| 5,623,810 A | 4/1997 | Dey et al. | |
| 5,708,023 A | 1/1998 | Modak et al. | |
| 5,722,992 A | 3/1998 | Goldmann | |
| 5,756,145 A | 5/1998 | Darouiche | |
| 5,772,640 A | 6/1998 | Modak et al. | |
| 5,804,628 A | 9/1998 | Busnel et al. | |
| 5,853,745 A * | 12/1998 | Darouiche | 424/423 |
| 5,868,244 A | 2/1999 | Ivanov et al. | |
| 5,889,075 A | 3/1999 | Roby et al. | |
| 5,902,283 A | 5/1999 | Darouiche | |
| 5,906,273 A | 5/1999 | Pohle et al. | |
| 5,906,825 A | 5/1999 | Seabrook et al. | |
| 5,945,153 A | 8/1999 | Dearnaley | |
| 5,965,610 A | 10/1999 | Modak et al. | |
| 5,968,207 A | 10/1999 | Li | |
| 5,972,008 A | 10/1999 | Kalinski et al. | |
| 5,985,934 A | 11/1999 | Gaffney et al. | |
| 5,997,815 A | 12/1999 | Anders et al. | |
| 6,021,625 A | 2/2000 | Cerwin et al. | |
| 6,034,010 A | 3/2000 | Cartwright et al. | |
| 6,037,386 A | 3/2000 | Modak et al. | |
| 6,047,815 A | 4/2000 | Cerwin et al. | |
| 6,083,208 A | 7/2000 | Modak et al. | |
| 6,087,415 A | 7/2000 | Vamderlaan et al. | |
| 6,093,414 A | 7/2000 | Capelli | |
| 6,106,505 A | 8/2000 | Modak et al. | |
| 6,135,272 A | 10/2000 | Sobel et al. | |
| 6,165,920 A | 12/2000 | Rubin et al. | |
| 6,200,583 B1 * | 3/2001 | Sibata et al. | 424/405 |
| 6,224,579 B1 | 5/2001 | Modak et al. | |
| 6,238,686 B1 | 5/2001 | Burrell et al. | |
| 6,260,699 B1 | 7/2001 | Kaplan et al. | |
| 6,315,788 B1 | 11/2001 | Roby | |
| 6,420,455 B1 | 7/2002 | Landgrebe et al. | |
| 6,475,434 B1 | 11/2002 | Darouiche | |
| 6,481,568 B1 | 11/2002 | Cerwin et al. | |
| 6,494,898 B1 | 12/2002 | Roby et al. | |
| 6,495,100 B1 | 12/2002 | Lin et al. | |
| 6,706,024 B2 | 3/2004 | Modak et al. | |
| 6,837,027 B2 | 1/2005 | Hickey | |
| 6,878,757 B2 | 4/2005 | Roby | |
| 6,915,623 B2 | 7/2005 | Dey et al. | |
| 6,916,480 B2 | 7/2005 | Anderson et al. | |
| 7,070,044 B2 * | 7/2006 | Rosenfeld | 206/63.3 |
| 7,215,401 B2 | 5/2007 | Ishiyama et al. | |
| 7,275,640 B2 * | 10/2007 | Bourne et al. | 206/219 |
| 7,513,093 B2 | 4/2009 | Scalzo et al. | |
| 7,651,661 B2 | 1/2010 | Raad et al. | |
| 8,069,980 B2 | 12/2011 | Stopek et al. | |
| 8,112,973 B2 | 2/2012 | Fischer et al. | |
| 8,133,437 B2 | 3/2012 | Scalzo et al. | |
| 8,156,718 B2 | 4/2012 | Scalzo et al. | |
| 2001/0010016 A1 | 7/2001 | Modak et al. | |
| 2001/0016589 A1 | 8/2001 | Modak et al. | |
| 2001/0024661 A1 | 9/2001 | Modak et al. | |
| 2002/0012760 A1 * | 1/2002 | Barry et al. | 428/35.7 |
| 2002/0055759 A1 | 5/2002 | Shibuya | |
| 2003/0108761 A1 | 6/2003 | Eddlemon | |
| 2003/0138347 A1 | 7/2003 | Lin | |
| 2004/0068293 A1 | 4/2004 | Scalzo et al. | |
| 2004/0068294 A1 | 4/2004 | Scalzo et al. | |
| 2004/0220614 A1 | 11/2004 | Scalzo et al. | |
| 2005/0033251 A1 | 2/2005 | Toreki et al. | |
| 2005/0101993 A1 | 5/2005 | Scalzo et al. | |
| 2006/0091035 A1 | 5/2006 | Scalzo et al. | |
| 2006/0231443 A1 | 10/2006 | Jonasson et al. | |
| 2008/0171972 A1 | 7/2008 | Stopek | |
| 2009/0301033 A1 | 12/2009 | Scalzo et al. | |
| 2010/0036359 A1 | 2/2010 | Stopek et al. | |
| 2010/0078336 A1 | 4/2010 | Reyhan et al. | |
| 2010/0116694 A1 | 5/2010 | Stopek et al. | |

(56) References Cited

U.S. PATENT DOCUMENTS

| | | | |
|---|---|---|---|
| 2010/0163435 A1 | 7/2010 | Fischer et al. | |
| 2012/0199502 A1 | 8/2012 | Scalzo et al. | |
| 2012/0227360 A1 | 9/2012 | Scalzo et al. | |
| 2012/0267263 A1 | 10/2012 | Fischer et al. | |
| 2013/0193008 A1 | 8/2013 | Reyhan et al. | |
| 2013/0193009 A1 | 8/2013 | Scalzo et al. | |
| 2013/0264226 A1 | 10/2013 | Prikril et al. | |

FOREIGN PATENT DOCUMENTS

| | | |
|---|---|---|
| CN | 2115083 U | 9/1992 |
| CN | 2190968 Y | 3/1995 |
| CN | 1125622 A | 7/1996 |
| EP | 0470443 A2 | 2/1992 |
| EP | 0471441 A1 | 2/1992 |
| EP | 0761243 A1 | 3/1997 |
| EP | 1159972 A2 | 12/2001 |
| GB | 809725 A | 3/1959 |
| JP | 49-111794 A | 10/1974 |
| JP | 8-164190 A | 6/1996 |
| JP | 10-504756 T | 5/1998 |
| JP | 11-500330 T | 1/1999 |
| JP | 2000-237289 A | 5/2000 |
| TW | 408011 B | 10/2000 |
| TW | 446822 B | 7/2001 |
| WO | 98/09667 A1 | 3/1998 |
| WO | 00/44414 A1 | 8/2000 |
| WO | 01/28601 A1 | 4/2001 |
| WO | 2004032704 A2 | 4/2004 |
| WO | 2008/045338 A2 | 4/2008 |
| WO | WO 2010/117802 A1 | 10/2010 |
| WO | 2011/008547 A1 | 1/2011 |

OTHER PUBLICATIONS

U.S. Appl. No. 10/367,497, filed Feb. 15, 2003.
U.S. Appl. No. 10/367,565, filed Feb. 15, 2003.
U.S. Appl. No. 10/603,317, filed Jun. 25, 2003.
U.S. Appl. No. 10/808,669, filed Mar. 25, 2004.
U.S. Appl. No. 11/301,365, filed Dec. 13, 2005.
U.S. Appl. No. 11/301,364, filed Dec. 13, 2005.
U.S. Appl. No. 12/415,600, filed Mar. 31, 2009.
U.S. Appl. No. 12/417,518, filed Apr. 2, 2009.
U.S. Appl. No. 12/493,992, filed Jun. 29, 2009.
PCT Application No. PCT/US2010/029233 filed Mar. 30, 2010.
U.S. Application No. PCT/US2010/040405 filed Jun. 29, 2010.
U.S. Appl. No. 13/419,377, filed Mar. 13, 2012.
U.S. Appl. No. 61/621,337, filed Apr. 6, 2012.
U.S. Appl. No. 13/501,063, filed Apr. 9, 2012.
U.S. Appl. No. 13/449,184, filed Apr. 17, 2012.
U.S. Appl. No. 13/727,340, filed Dec. 26, 2012.
Database EMBASE on STN, AN 2003062. Barbolt T.A. "Chemistry and Safety of Triclosan, and Its Use as an Antimicrobial Coating on Coated VICRYL. Plus Antibacterial Suture (Coated Polyglactin 910 Suture with Triclosan)". Surgical Infections, May 2002, vol. 3, No. 3, Supplement 1, pp. S-45-S53, see abstract.
Database ACS on STN, AN 133: 366471. Anuzis et al. "Acetate Antimicrobial Threads". LT 4568 B, Oct. 25, 1999, abstract.
Josephine J. Braid et al., "The antibacterial activity of triclosan-impregnated storage boxes against *Staphylococcus aureus, Escherichia colil, Pseudomonas aeruginosa, Bacillus cereus* and *Shewanella putrefaciens* in conditions simulating domestic use" Journal of Antimocrobial Chemotherapy (2002) vol. 49 pp. 87-94.
International Search Report of International Application No. PCT/US2010/040405.
Bhargava, H. et al "American Journal of Infection Control" pp. 209-218, Jun. 1996. Abstract only.
International Search Report of International Application No. PCT/US2010/029233.
Robert Cerwin, U.S. Appl. No. 60/416,114, filed Oct. 4, 2002.
Howard Scalzo, U.S. Appl. No. 10/367,497, filed Feb. 15, 2003.
Howard Scalzo, U.S. Appl. No. 10/367,565, filed Feb. 15, 2003.
Howard Scalzo, U.S. Appl. No. 10/603,317, filed Jun. 25, 2003.
Howard Scalzo, U.S. Appl. No. 10/808,669, filed Mar. 25, 2004.
Howard Scalzo, U.S. Appl. No. 11/301,365, filed Dec. 13, 2005.
Howard Scalzo, U.S. Appl. No. 11/301,364, filed Dec. 13, 2005.
Mehmet Reyhan, U.S. Appl. No. 12/415,600, filed Mar. 31, 2009.
Howard Scalzo, U.S. Appl. No. 12/417,518, filed Apr. 2, 2009.
Jerry Fischer, U.S. Appl. No. 12/493,992, filed Jun. 29, 2009.
Mehmet Reyhan, PCT Application No. PCT/US2010/029233 filed Mar. 30, 2010.
Jerry Fischer, PCT Application No. PCT/US2010/040405 filed Jun. 29, 2010.
Howard Scalzo, U.S. Appl. No. 13/419,377, filed Mar. 13, 2012.
Michael David Prikril, U.S. Appl. No. 61/621,337, filed Apr. 6, 2012.
Jerry Fischer, U.S. Appl. No. 13/501,063, filed Apr. 9, 2012.
Howard Scalzo, U.S. Appl. No. 13/449,184, filed Apr. 17, 2012.
Michael David Prikril, U.S. Appl. No. 13/727,340, filed Dec. 26, 2012.
Mehmet Reyhan, U.S. Appl. No. 13/801,819, filed Mar. 13, 2013.
Howard Scalzo, U.S. Appl. No. 13/802,007, filed Mar. 13, 2013.

* cited by examiner

PACKAGED ANTIMICROBIAL MEDICAL DEVICE AND METHOD OF PREPARING SAME

CROSS-REFERENCE TO PRIOR APPLICATIONS

This application is a Divisional of U.S. Ser. No. 12/415,600, filed on Mar. 31, 2009, which is a continuation-in-part of U.S. Ser. No. 11/301,365, filed on Dec. 13, 2005 (now U.S. Pat. No. 7,513,093), and U.S. Ser. No. 11/301,364, filed on Dec. 13, 2005 (now U.S. Pat. No. 8,133,437), each of which is a continuation-in-part of U.S. Ser. No. 10/808,669, filed on Mar. 25, 2004, which is a continuation-in-part of U.S. Ser. No. 10/603,317 filed on Jun. 25, 2003, which is a continuation-in-part of U.S. Ser. No. 10/367,497 filed on Feb. 15, 2003, which claimed the benefit of U.S. Provisional Application No. 60/416,114 filed on Oct. 4, 2002, the contents of each are hereby incorporated by reference in their entirety.

FIELD OF THE INVENTION

The present invention relates to a packaged antimicrobial medical device and its methods of making.

BACKGROUND OF THE INVENTION

Each year, patients undergo a vast number of surgical procedures in the United States. Current data shows about twenty-seven million procedures are performed per year. Post-operative or surgical site infections ("SSIs") occur in approximately two to three percent of all cases. This amounts to more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

Implantable medical devices that contain antimicrobial agents applied to or incorporated within have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-tricloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated. It is not apparent from the application at what temperature the sterilized, coated catheters were stored.

Most implantable medical devices are manufactured, sterilized and contained in packages until opened for use in a surgical procedure. During surgery, the opened package containing the medical device, packaging components contained therein, and the medical device, are exposed to the operating room atmosphere, where bacteria from the air may be introduced. Incorporating antimicrobial properties into the package and/or the packaging components contained therein substantially prevents bacterial colonization on the package and components once the package has been opened. The antimicrobial package and/or packaging components in combination with the incorporation of antimicrobial properties onto the medical device itself would substantially ensure an antimicrobial environment about the sterilized medical device.

SUMMARY OF THE INVENTION

The present invention relates to packaged antimicrobial medical devices and methods for preparing such packaged medical devices. In accordance with embodiments of the present invention, a containment compartment is formed from a polymeric resin comprising a polymeric material and an antimicrobial agent. A medical device is positioned within the containment compartment and covered with an outer package cover. Upon subjecting the medical device so packaged to sufficient conditions, a portion of the antimicrobial agent transfers from the containment compartment to the medical device. The transfer of the antimicrobial agent is in an amount sufficient to inhibit bacterial growth on and about the medical device, the inner surface of the outer package cover and the containment compartment.

In one embodiment, an effective amount of the antimicrobial agent is transferred from the containment compartment to the medical device and the inner surface of the outer package cover during an ethylene oxide sterilization process.

In another embodiment, the medical device may be substantially free of antimicrobial agent.

In yet another embodiment, the medical device may be coated with an antimicrobial agent.

In still yet another embodiment, the medical device so packaged is subjected to conditions sufficient to vapor transfer an effective amount of the antimicrobial agent by a process that includes the steps of placing the outer package cover, the containment compartment, and the medical device in a sterilization unit; heating the sterilization unit to a first temperature; adjusting the pressure in the sterilization unit to a first pressure value; injecting steam into the sterilization unit to expose the outer package cover, the containment compartment and the medical device to water vapor for a first period of time; adjusting the pressure within the sterilization unit to a second pressure value; introducing a chemical sterilization agent into the sterilization unit; maintaining the chemical sterilization agent in the sterilization unit for a second period of time to render a sufficient amount of microorganisms within the outer package cover non-viable; removing residual moisture and chemical sterilization agent from the medical device; and drying the packaged medical device to a desired moisture level.

In a further embodiment, the containment compartment may be molded from a polymeric resin that includes a polymeric material and an antimicrobial agent, the antimicrobial agent further including at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

In still further embodiment, the containment compartment is molded by injection molding.

The present invention is also directed to a method for preparing a packaged antimicrobial medical device, which includes the steps of providing a containment compartment molded from a polymeric resin comprising a polymeric material and an antimicrobial agent; positioning a medical device within the containment compartment, the medical device comprising one or more surfaces; covering the containment compartment having the medical device in an outer package cover having an inner surface; and subjecting the outer package cover, the containment compartment and the medical device to time, temperature and pressure conditions sufficient to vapor transfer an effective amount of the antimicrobial agent from the containment compartment to the medical device, while retaining an effective amount of the antimicrobial agent on the containment compartment, thereby substantially inhibiting bacterial colonization on the medical device and the containment compartment.

The present invention also relates to packaged antimicrobial sutures and methods for preparing such packaged sutures. In accordance therewith, a containment compartment is formed from a polymeric resin comprising a polymeric material and an antimicrobial agent. A suture is positioned within the containment compartment and covered with an outer package cover. Upon subjecting the suture so packaged to sufficient conditions, a portion of the antimicrobial agent transfers from the containment compartment to the suture. The transfer of the antimicrobial agent is in an amount sufficient to inhibit bacterial growth on and about the suture, the inner surface of the outer package cover and the containment compartment.

The present invention is also directed to a method for preparing a packaged antimicrobial suture. The method includes the steps of providing a containment compartment molded from a polymeric resin comprising a polymeric material and an antimicrobial agent; positioning a suture within the containment compartment, the suture comprising one or more surfaces; covering the containment compartment having the suture in an outer package cover having an inner surface; and subjecting the outer package cover, the containment compartment and the suture to time, temperature and pressure conditions sufficient to vapor transfer an effective amount of the antimicrobial agent from the containment compartment to the suture, while retaining an effective amount of the antimicrobial agent on the containment compartment, thereby substantially inhibiting bacterial colonization on the suture and the containment compartment.

In one embodiment, an effective amount of the antimicrobial agent is transferred from the containment compartment to the suture and the inner surface of the outer package cover during an ethylene oxide sterilization process.

In another embodiment, the suture may be substantially free of antimicrobial agent.

In yet another embodiment, the suture may be coated with an antimicrobial agent.

In still yet another embodiment, the suture so packaged is subjected to conditions sufficient to vapor transfer an effective amount of the antimicrobial agent by a process that includes the steps of covering the outer package cover and the suture in a sterilization unit; heating the sterilization unit to a first temperature; adjusting the pressure in the sterilization unit to a first pressure value; injecting steam into the sterilization unit to expose the outer package cover, the containment compartment and the suture to water vapor for a first period of time; adjusting the pressure within the sterilization unit to a second pressure value; introducing a chemical sterilization agent into the sterilization unit; maintaining the chemical sterilization agent in the sterilization unit for a second period of time to render a sufficient amount of microorganisms on the inner surface of the outer package cover non-viable; removing residual moisture and chemical sterilization agent from the suture; and drying the packaged suture to a desired moisture level.

In a further embodiment, the containment compartment may be molded from a polymeric resin that includes a polymeric material and an antimicrobial agent, the antimicrobial agent further including at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

In still further embodiment, the containment compartment is molded by injection molding.

BRIEF DESCRIPTION OF THE DRAWINGS

The invention is further explained in the description that follows with reference to the drawings illustrating, by way of non-limiting examples, various embodiments of the invention wherein.

DETAILED DESCRIPTION OF EMBODIMENTS OF THE INVENTION

Reference is now made to FIGS. 1-6 wherein like numerals are used to designate like elements throughout.

Packaged Antimicrobial Medical Device

Figure 1:
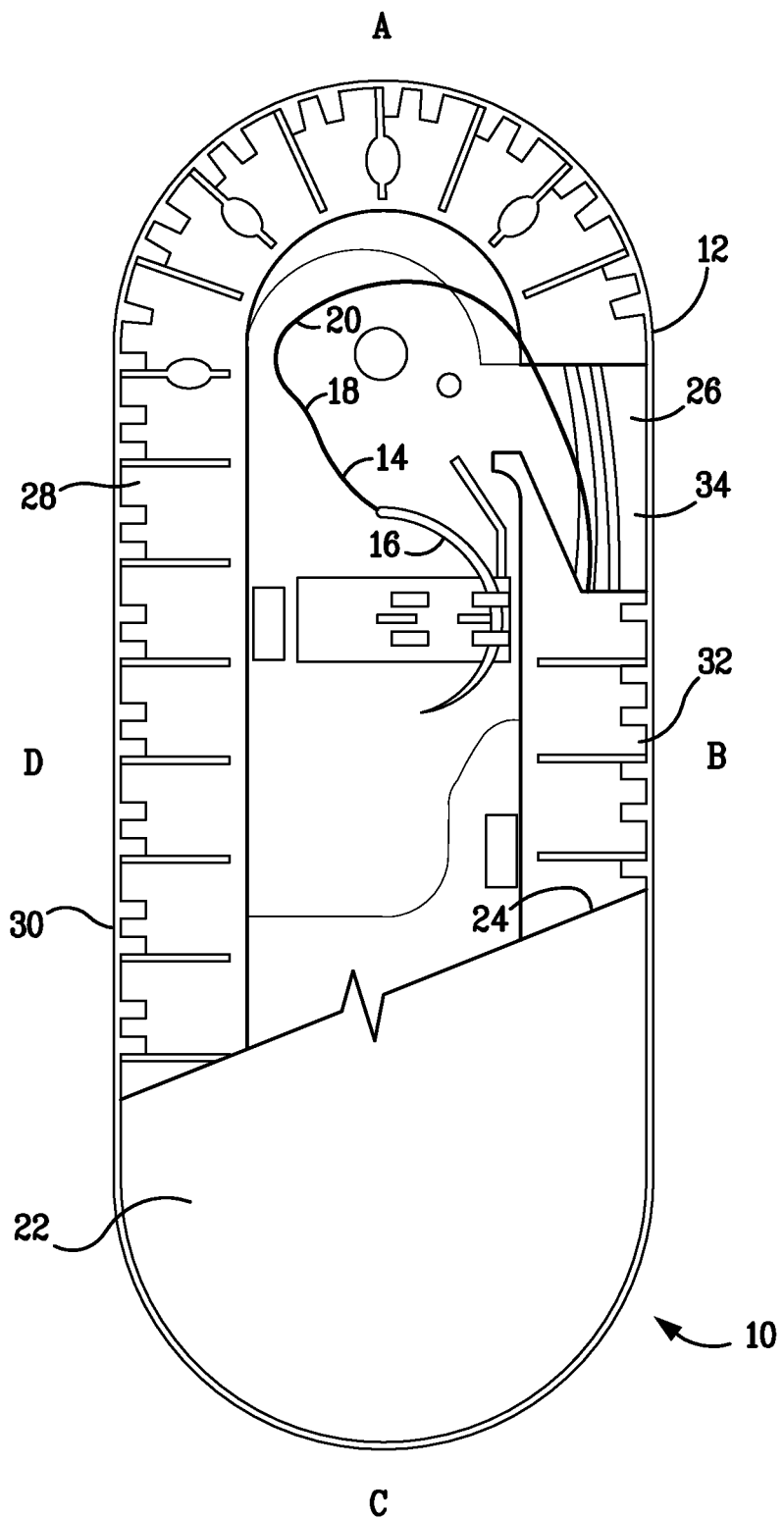
FIG. 1 is a top plan view of a packaged antimicrobial medical device of the type disclosed herein, wherein the medical device is a single needle and suture.

Referring now to FIG. 1, one embodiment of the packaged antimicrobial medical device 10 includes a containment compartment 12 molded from a polymeric resin comprising a polymeric material and an antimicrobial agent. A medical device 14, which may be a needle 16 and suture 18 having one or more surfaces 20 is positioned within the containment compartment 12. The medical device 14 may be initially substantially free of antimicrobial agent or, in another embodiment, may be coated with an antimicrobial agent. An outer package cover 22 may be employed, the outer package cover 22 having an inner surface 24 for placing the containment compartment having said medical device therein.

The containment compartment 12 of packaged antimicrobial medical device 10 includes a base member 26 and a channel cover member 28. Base member 26 includes a top side, bottom side, and an outer periphery 30. As shown, an outer package cover 22 may be positioned upon channel cover member 28 and within outer periphery 30, to fully enclose medical device 14. The base member 26 may be a substantially flat substantially oval shaped member having a longitudinal axis. While in the case of packaged sutures, it may be desired that the base member 26 of packaged antimicrobial medical device 10 be oval shaped, other configurations can be used including circular, polygonal, square with rounded corners, and the like and combinations thereof and equivalents thereof. Channel cover 28 includes a top side, bottom side, periphery 32 and longitudinal axis.

The packaged antimicrobial medical device 10 of the present invention may be assembled in the following manner. Base member 26 is aligned with channel cover member 28 so that rivets, if employed are in alignment with the rivet receiving holes, and locating pins, if employed, are in alignment with corresponding openings. Also, winding pin openings, if employed, are aligned with corresponding openings. Then, channel cover member 28 is then mounted to base member 26 such that rivets, if employed, are inserted into and through corresponding holes and locating pins, if employed are inserted through corresponding holes 130. The ends of the rivets, if employed, may be spread by using conventional techniques such as heating, ultrasonic treatments, and the like so that the channel cover member 28 is firmly affixed to the base member 26. In this embodiment, when containment compartment 12 is so formed, a channel 34 is formed, which may advantageously house a wound suture 18.

Further details regarding the construction and geometry of the containment compartments and packages formed therefrom are more fully described in U.S. Pat. Nos. 6,047,815; 6,135,272 and 6,915,623, the contents of each are hereby incorporated by reference in their entirety for all that they disclose.

Containment compartment 12 of the present invention may be manufactured from conventional moldable materials. It is especially preferred to use polyolefin materials such as polyethylene and polypropylene, other thermoplastic materials, and polyester materials such as nylon, and equivalents thereof. Preferably the containment compartments 12 of the present invention may be injection molded, however, they may be formed by other conventional processes and equivalents thereof including thermo-forming. If desired, the packages may be manufactured as individual assemblies or components which are then assembled.

The sutures and needles that can be packaged in the packages 10 of the present invention include conventional surgical needles and conventional bioabsorbable and nonabsorbable surgical sutures and equivalents thereof. The packages of the present invention are useful to package small diameter sutures which were previously difficult to package in tray packages because of removal or hang-up problems upon withdrawal of such suture from the packages. These problems have been overcome using the packages of the present invention.

The polymeric material for use in forming the resin for use in the molding of the containment compartment 12 may be selected from conventional thermoplastic materials, such as polyethylene and polypropylene, from polyesters, such as polyvinyl chloride, polypropylene, polystyrene, polyethylene, polyesters, including poly(ethylene terephthalate) (PET), nylon, and equivalents and blends thereof. In one embodiment, high density polyethylene (HDPE) may be employed as the polymeric material. The packages 10 of the present invention may be injection molded, however, the containment compartments 12 may be formed by other conventional processes and equivalents thereof including thermo-forming.

As indicated above, the polymeric resin used to mold containment compartment 12 also includes an antimicrobial agent. Suitable antimicrobial agents may be selected from, but are not limited to, halogenated hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, as described in U.S. Pat. No. 3,629,477, and represented by the following formula:

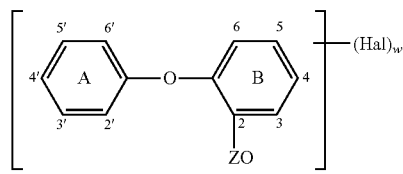

In the above formula, each Hal represents identical or different halogen atoms, Z represents hydrogen or an acyl group, and w represents a positive whole number ranging from 1 to 5, and each of the benzene rings, but preferably ring A can also contain one or several lower alkyl groups which may be halogenated, a lower alkoxy group, the allyl group, the cyano group, the amino group, or lower alkanoyl group. Preferably, methyl or methoxy groups are among the useful lower alkyl and lower alkoxy groups, respectively, as substituents in the benzene rings. A halogenated lower alkyl group, trifluoromethyl group is preferred.

Antimicrobial activity similar to that of the halogen-o-hydroxydiphenyl ethers of the above formula is also attained using the O-acyl derivatives thereof which partially or completely hydrolyze under the conditions for use in practice. The esters of acetic acid, chloroacetic acid, methyl or dimethyl carbamic acid, benzoic acid, chlorobenzoic acid, methylsulfonic acid and chloromethylsulfonic acid are particularly suitable.

One particularly preferred antimicrobial agent within the scope of the above formula is 2,4,4'-trichloro-2'-hydroxydiphenyl ether, commonly referred to as triclosan (manufactured by Ciba Geigy under the trade name Irgasan DP300 or Irgacare MP). Triclosan is a white powdered solid with a slight aromatic/phenolic odor. As may be appreciated, it is a chlorinated aromatic compound which has functional groups representative of both ethers and phenols. Triclosan is only slightly soluble in water, but soluble in ethanol, diethyl ether, and stronger basic solutions such as 1 M sodium hydroxide. Triclosan can be made from the partial oxidation of benzene or benzoic acid, by the cumene process, or by the Raschig process. It can also be found as a product of coal oxidation Triclosan is a broad-spectrum antimicrobial agent that has been used in a variety of products, and is effective against a number of organisms commonly associated with 5515. Such microorganisms include, but are not limited to, genus *Staphylococcus*, *Staphylococcus epidermidis*, *Staphylococcus aureus*, methicillin-resistant *Staphylococcus epidermidis*, methicillin-resistant *Staphylococcus aureus*, and combinations thereof.

In addition to the antimicrobial agents described above, the medical device optionally may have a biocide, a disinfectant and/or an antiseptic, including but not limited to alcohols such as ethanol and isopropanol; aldehydes such as glutaraldehyde and formaldehyde; anilides such as triclorocarbanilide; biguanides such as chlorhexidine; chlorine-releasing agents such as sodium hypochlorite, chlorine dioxide and acidified sodium chlorite; iodine-releasing agents such as povidone-iodine and poloxamer-iodine; metals such as silver nitrate, silver sulfadiazine, other silver agents, copper-8-quinolate and bismuth thiols; peroxygen compounds such as hydrogen peroxide and peracetic acid; phenols; quaternary ammonium compounds such as benzalkonium chloride, cetrimide and ionenes-polyquaternary ammonium compounds. The medical device optionally may have antibiotics, including but not limited to penicillins such as amoxicillin, oxacillin and piperacillin; cephalosporins parenteral such as cefazolin, cefadroxil, cefoxitin, cefprozil, cefotaxime and cefdinir;

monobactams such as aztreonam; beta-lactamase inhibitors such as clavulanic acid sulbactam; glycopeptide such as vancomycin; polymixin; quinolones such as nalidixic acid, ciprofloxacin and levaquin; metranidazole; novobiocin; actinomycin; rifampin; aminoglycosides such as neomycin and gentamicin; tetracyclines such as doxycycline; chloramphenicol; macrolide such as erythromycin; clindamycin; sulfonamide such as sulfadiazine; trimethoprim; topical antibiotics; bacitracin; gramicidin; mupirocin; and/or fusidic acid. Optionally, the medical device may have antimicrobial peptides such as defensins, magainin and nisin; lytic bacteriophage; surfactants; adhesion blockers such as antibodies, oligosaccharides and glycolipids; oligonucleotides such as antisense RNA; efflux pump inhibitors; photosensitive dyes such as porphyrins; immune modulators such as growth factors, interleukins, interferons and synthetic antigens; and/or chelators such as EDTA, sodium hexametaphosphate, lactoferrin and transferrin.

To form the polymeric resin used to mold containment compartment 12, pellets of an antibacterial agent, such as triclosan, 4% by weight, may be mechanically mixed with pellets of a titanium dioxide colorant mixture, 3% by weight, and pellets of a standard mold release agent, such as ampacent, 3% by weight. The mixture so formed may be extruded using conventional equipment to form a colorant mixture. The extruded triclosan/colorant/mold-release agent mixture may then be compounded with a high density polyethylene (HDPE) polymer to form the resin to be used in manufacturing containment compartments, such as suture holding trays. The resultant polymer resin can then be injection molded to form two-component containment compartments 12.

One embodiment of the packaged antimicrobial medical device includes a containment compartment for securing the medical device that resides within, the containment compartment molded from a polymeric resin comprising a polymeric material and an antimicrobial agent. A medical device comprising one or more surfaces is positioned within the containment compartment. An outer package cover having an inner surface may be employed to cover the containment compartment and suture.

In one embodiment, the medical device positioned within the containment compartment may be initially substantially free of antimicrobial agent. By "initially substantially free" is meant that the medical device so positioned within the containment compartment has not been treated or coated with an agent having efficacy as an antimicrobial agent prior to positioning within the containment compartment. In another embodiment, the medical device positioned within the containment compartment may be coated with an antimicrobial agent. By "coated with an antimicrobial agent" is meant that the medical device so positioned within the containment compartment has been treated or coated with an agent having efficacy as an antimicrobial agent prior to positioning within the containment compartment.

As will be discussed in more detail below, prior to use, the packaged antimicrobial medical device, which includes the outer package cover, containment compartment and medical device may be subjected to time, temperature and pressure conditions sufficient to vapor transfer an effective amount of antimicrobial agent from the containment compartment to the medical device and the inner surface of the outer package cover, while retaining an effective amount of said antimicrobial agent on the containment compartment, thereby substantially inhibiting bacterial colonization on the medical device and the containment compartment. This vapor transfer mechanism can also increase the antimicrobial efficacy for medical devices that have been treated or coated with an agent having efficacy as an antimicrobial agent prior to positioning within the containment compartment when the container compartment has been formed using the resins described herein. In one embodiment, the effective amount of said antimicrobial agent transferred from the containment compartment to the medical device and the inner surface of the outer package cover is transferred during an ethylene oxide sterilization process.

In another embodiment, the packaged medical device includes a containment compartment molded from a polymeric resin comprising a polymeric material and an antimicrobial agent; a suture comprising one or more surfaces and positioned within the containment compartment; and an outer package cover having an inner surface for covering the containment compartment having the suture therein. In one embodiment, the suture positioned within the containment compartment is substantially free of antimicrobial agent. In another embodiment, the suture positioned within the containment compartment is coated with an antimicrobial agent. In still another embodiment, the antimicrobial agent is selected from the group consisting of halogenated hydroxyl ethers, acyloxydiphenyl ethers, and combinations thereof.

As with the packaged medical device disclosed herein, prior to use, the packaged antimicrobial suture, which includes the outer package cover, containment compartment and suture may be subjected to time, temperature and pressure conditions sufficient to vapor transfer an effective amount of antimicrobial agent from the containment compartment to the suture and the inner surface of the outer package cover, while retaining an effective amount of said antimicrobial agent on the containment compartment, thereby substantially inhibiting bacterial colonization on the suture and the containment compartment. This vapor transfer mechanism can also increase the antimicrobial efficacy for sutures that have been treated or coated with an agent having efficacy as an antimicrobial agent prior to positioning within the containment compartment when the container compartment has been formed using the resins described herein. In one embodiment, the effective amount of said antimicrobial agent transferred from the containment compartment to the medical device and the inner surface of the outer package cover is transferred during an ethylene oxide sterilization process.

The medical devices described herein are generally implantable medical devices, including but not limited to mono and multifilament sutures, surgical meshes such as hernia repair mesh, hernia plugs, brachy seed spacers, suture clips, suture anchors, adhesion prevention meshes and films, and suture knot clips. Also included are implantable medical devices that are absorbable and non-absorbable. An absorbable polymer is defined as a polymer that, when exposed to physiological conditions, will degrade and be absorbed by the body over a period of time. Absorbable medical devices typically are formed from generally known, conventional absorbable polymers including, but not limited to, glycolide, lactide, co-polymers of glycolide, or mixtures of polymers, such as polydioxanone, polycaprolactone and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Examples of absorbable medical device include mono and multifilament sutures. The multifilament suture includes sutures wherein a plurality of filaments is formed into a braided structure. Examples of non-absorbable medical devices include mono and multifilament sutures, surgical meshes such as hernia repair mesh, hernia plugs and brachy seed spacers, which may be polymeric or nonpolymeric.

For embodiments of the present invention that contemplate the use of a medical device that will be treated or coated with an agent having efficacy as an antimicrobial agent prior to packaging, it is advantageous to use a coating composition as a vehicle for delivering the antimicrobial agent to the surface of the device where such coating already is used conventionally in the manufacture of the device, such as, for example, absorbable and non-absorbable multifilament sutures. Examples of medical devices, as well as coatings that may be applied thereto, may be found in U.S. Pat. Nos. 4,201,216; 4,027,676; 4,105,034; 4,126,221; 4,185,637; 3,839,297; 6,260,699; 5,230,424; 5,555,976; 5,868,244; and 5,972,008; each of which is hereby incorporated herein in its entirety. As disclosed in U.S. Pat. No. 4,201,216, the coating composition may include a film-forming polymer and a substantially water-insoluble salt of a $C_6$ or higher fatty acid. As another example, an absorbable coating composition that may be used for an absorbable medical device may include poly(alkylene oxylates) wherein the alkylene moieties are derived from $C_6$ or mixtures of $C_4$ to $C_{12}$ diols, which is applied to a medical device from a solvent solution, as disclosed in U.S. Pat. No. 4,105,034. The coating compositions of the present invention may include a polymer or co-polymer, which may include lactide and glycolide, as a binding agent. The compositions may also include calcium stearate, as a lubricant, and an antimicrobial agent. Medical devices not conventionally employing a coating in the manufacturing process, however, also may be coated with a composition comprising an antimicrobial agent. The coating may be applied to the device by, for example, dip coating, spray coating, suspended drop coating, or any other conventional coating means.

Absorbable medical devices are moisture sensitive, that is, they are devices that will degrade if exposed to moisture in the atmosphere or in the body. It is known by those of ordinary skill in the art that medical devices made from absorbable polymers may deteriorate and lose their strength if they come into contact with water vapor prior to use during surgery. For instance, the desirable property of in vivo tensile strength retention for sutures will be rapidly lost if the sutures are exposed to moisture for any significant period of time prior to use. Therefore, it is desirable to use a hermetically sealed package for absorbable medical devices. A hermetically sealed package is defined herein to mean a package made of a material that serves as both a sterile barrier and a gas barrier, i.e., prevents or substantially inhibits moisture and gas permeation.

Materials useful for constructing the package for absorbable medical devices, for example, include single and multi-layered conventional metal foil products, often referred to as heat-sealable foils. These types of foil products are disclosed in U.S. Pat. No. 3,815,315, which is hereby incorporated by reference in its entirety. Another type of foil product that may be utilized is a foil laminate referred to in the field of art as a peelable foil. Examples of such peelable foil and substrates are disclosed in U.S. Pat. No. 5,623,810, which is hereby incorporated by reference in its entirety. If desired, conventional non-metallic polymer films in addition to or in lieu of metal foil may be used to form the package for absorbable medical devices. Such films are polymeric and may include conventional polyolefins, polyesters, acrylics and the like, combinations thereof and laminates. These polymeric films substantially inhibit moisture and oxygen permeation and may be coated with conventional coatings, such as, for example, mineral coatings that decrease or reduce gas intrusion. The package may comprise a combination of polymer and metal foils, particularly a multi-layer polymer/metal-foil composite.

Nonabsorbable medical devices may be packaged in any of the materials described above. In addition, it is desirable to package nonabsorbable medical devices in a package made of a material that serves as a sterile barrier, such as a porous material, i.e., medical grade paper, or a polymeric film that is permeable to moisture and gas, i.e., Tyvek® film, manufactured by DuPont and made from high-density polyethylene fibers.

Packages for surgical needles, sutures and combinations including the suture and a surgical needle typically comprise a suture tray as the containment compartment, for securely holding the suture and/or surgical needle in place. Types other than that shown in FIG. 1 are contemplated herein. These other designs typically include a molded plastic tray having a central floor surrounded by an outer winding channel for receiving and retaining a suture, e.g., an oval channel. The containment compartment may further include a medical grade paper or plastic cover that may be mounted to the top of the winding channel, or the molded plastic tray may have molded retainer elements, in order to maintain the suture in the channel. Containment compartments having winding channels are illustrated in the following, each of which is hereby incorporated by reference in its entirety: U.S. Pat. Nos. 4,967,902, 5,213,210 and 5,230,424.

Microorganisms of the genus Staphylococcus are the most prevalent of all of the organisms associated with device-related surgical site infection. *S. aureus* and *S. epidermidis* are commonly present on patients' skin and as such are introduced easily into wounds. One of the most efficacious antimicrobial agents against *Staphylococcus* is 2,4,4'-trichloro-2'-hydroxydiphenyl ether. This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrase "an amount sufficient to substantially inhibit bacterial colonization" as used herein is defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the anti-microbial agent diffuses through the medium, and as long as the concentration of the antimicrobial agent is above the minimum inhibitory concentration (MIC), none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Alternatively, the concentration of triclosan present on the surface of a medical device such as a coated suture may be greater than about 0.01 ppm (wt./wt. coating) or between about 30 ppm to 5,000 ppm (wt./wt. suture). The concentration of triclosan on the surface of package or containment compartment may be between about 5 ppm to 5,000 ppm (wt./wt. package or compartment). For other particular applications, however, higher amounts of antimicrobial agent may be useful and should be considered well within the scope of the present invention Method for Making a Packaged Antimicrobial Medical Device In accordance with various methods of the present invention, a containment compartment is provided that has been molded from a polymeric resin comprising a polymeric material and an antimicrobial agent. In one embodiment, a medical device that is initially substantially free of an antimicrobial agent may be provided. The medical device is positioned within the containment compartment. The containment compartment having the suture is covered with an outer package cover having an inner surface. Subsequently, the outer package cover, the containment compartment and the medical device are subjected to time, temperature and pressure conditions sufficient to vapor transfer a portion of the antimicrobial agent from the containment compartment to the medical device and the inner surface of the outer package cover.

The rate of transfer of an antimicrobial agent such as triclosan from the containment compartment to the medical device and the inner surface of the outer package cover is substantially dependent upon the time, temperature and pressure conditions under which the package with the containment compartment and the medical device is processed, stored and handled. For example, it has been observed that triclosan is capable of transferring from a suture to a containment compartment (in a closed vial at atmospheric pressure) when the temperature is maintained at 55° C. over a period of time. The conditions to effectively vapor transfer an antimicrobial agent such as triclosan include a closed environment, atmospheric pressure, a temperature of greater than 40° C., for a period of time ranging from 4 to 8 hours. Also included are any combinations of pressure and temperature to render a partial pressure for the antimicrobial agent that is the same as the partial pressure rendered under the conditions described above, in combination with a period of time sufficient to render an effective amount or concentration of the antimicrobial agent on the containment compartment, medical device and the inner surface of the outer package cover, i.e., the minimum inhibitory concentration (MIC) or greater. Specifically, it is known to one of ordinary skill that if the pressure is reduced, the temperature may be reduced to effect the same partial pressure. Alternatively, if the pressure is reduced, and the temperature is held constant, the time required to render an effective amount or concentration of the antimicrobial agent on the containment compartment, medical device and the inner surface of the outer package cover may be shortened. While a portion of the antimicrobial agent is transferred from the containment compartment to the medical device and the inner surface of the outer package cover during this process, a second portion is retained on the surface of the containment compartment. Accordingly, after the transfer, the medical device and the package and/or the containment compartment contain the antimicrobial agent in an amount effective to substantially inhibit bacterial colonization thereon and thereabout.

Medical devices typically are sterilized to render microorganisms located thereon non-viable. In particular, sterile is understood in the field of art to mean a minimum sterility assurance level of $10^{-6}$. Examples of sterilization processes are described in U.S. Pat. Nos. 3,815,315; 3,068,864; 3,767,362; 5,464,580; 5,128,101; and 5,868,244; each of which is incorporated herein in its entirety. Specifically, absorbable medical devices may be sensitive to radiation and heat. Accordingly, it may be desirable to sterilize such devices using conventional sterilant gases or agents, such as, for example, ethylene oxide gas.

An ethylene oxide sterilization process is described below, since the time, temperature and pressure conditions sufficient to vapor transfer a portion of the antimicrobial agent from the medical device to the package and/or containment compartment, are present in an ethylene oxide sterilization process. However the time, temperature and pressure conditions sufficient to vapor transfer the antimicrobial agent from the medical device to the package and/or containment compartment may be effected alone or in other types of sterilization processes, and are not limited to an ethylene oxide sterilization process or to sterilization processes in general.

As discussed above, absorbable medical devices are sensitive to moisture and are therefore often packaged in hermetically sealed packages, such as sealed foil packages. However, sealed foil packages are also impervious to sterilant gas. In order to compensate for this and utilize foil packages in ethylene oxide gas sterilization processes, processes have been developed using foil packages having gas permeable or pervious vents (e.g., TYVEK® polymer). The gas permeable vents are mounted to an open end of the package and allow the passage of air, water vapor and ethylene oxide into the interior of the package. After the sterilization process is complete, the package is sealed adjacent to the vent, and the vent is cut away or otherwise removed, thereby producing a gas impervious hermetically sealed package. Another type of foil package having a vent is a pouch-type package having a vent mounted adjacent to an end of the package, wherein the vent is sealed to one side of the package creating a vented section. After the sterilization process is complete the package is sealed adjacent to the vent, and the package is cut away for the vented section The medical device may be substantially free of, and preferably completely free of, antimicrobial agent prior to the transfer of the antimicrobial agent from the containment compartment to the medical device and the inner surface of the outer package cover. The medical device may first be placed within the containment compartment, if necessary, and then within the package. After the peripheral seal and side seals have been formed in the package, the packaged medical device may be placed into a conventional ethylene oxide sterilization unit. If the package is a foil package, the gas permeable vents described above may be used. Prior to the start of the cycle, the sterilization unit may be heated to an internal temperature of about 25° C. The sterilization unit is maintained about 22 to 37° C. throughout the humidification and sterilization cycles. Next, a vacuum may be drawn on the sterilization unit to achieve a vacuum of approximately 1.8 to 6.0 kPa. In a humidification cycle, steam then may be injected to provide a source of water vapor for the product to be sterilized. The packaged medical devices may be exposed to water vapor in the sterilization unit for a period of time of about 60 to 90 minutes. Times may vary, however, depending upon the medical device being sterilized.

Following this humidification portion of the cycle, the sterilization unit may be pressurized by the introduction of dry inert gas, such as nitrogen gas, to a pressure of between about 42 and 48 kPa. Once the desired pressure is reached, pure ethylene oxide may be introduced into the sterilization unit until the pressure reaches about 95 kPa. The ethylene oxide may be maintained for a period of time effective to sterilize the packaged medical device. For example, the ethylene oxide may be maintained in the sterilization unit for about 360 to about 600 minutes for surgical sutures. The time required to sterilize other medical devices may vary depending upon the type of product and the packaging. The ethylene oxide then may be evacuated from the sterilization unit and the unit may be maintained under vacuum at a pressure of approximately 0.07 kPa for approximately 150 to 300 minutes in order to remove residual moisture and ethylene oxide from the sterilized packaged medical devices. The pressure in the sterilization unit may be returned to atmospheric pressure.

The following stage of the process is a drying cycle. The packaged medical device may be dried by exposure to dry nitrogen and vacuum over a number of cycles sufficient to effectively remove residual moisture and water vapor from the packaged medical device to a preselected level. During these cycles, the packaged medical device may be subjected to a number of pressure increases and decreases, at temperatures greater than room temperature. Specifically, the jacket temperature of the drying chamber may be maintained at a temperature of between approximately 53° C. to 57° C. throughout the drying cycle. Higher temperatures, however, may be employed, such as about 65° C. to 70° C. for sutures, and higher depending upon the medical device being sterilized. A typical drying cycle includes the steps of increasing the pressure with nitrogen to approximately 100 kPa, evacuating the chamber to a pressure of approximately 0.07 kPa over a period of 180 to 240 minutes, reintroducing nitrogen to a pressure of 100 kPa and circulating the nitrogen for approximately 90 minutes, evacuating the chamber to a pressure of approximately 0.01 kPa over a period of approximately 240 to 360 minutes and maintaining a pressure of not more than 0.005 kPa for an additional 4 to 96 hours. At the end of the humidification, sterilization and drying cycles, which takes typically about 24 hours, the vessel is returned to ambient pressure with dry nitrogen gas. Once drying to the preselected moisture level is complete, the packaged medical device may be removed from the drying chamber and stored in a humidity controlled storage area.

Upon completion of the sterilization process, the antimicrobial medical device, the outer package cover and the containment compartment have thereon an amount of the antimicrobial agent effective to substantially inhibit colonization of bacteria on or adjacent the antimicrobial device, the package and/or the containment compartment.

Example 1

In preparation for forming a containment compartment of the type disclosed herein, pellets of the antibacterial agent triclosan, 4% by weight, were mechanically mixed with pellets of a titanium dioxide colorant mixture, 3% by weight, and pellets of a standard mold release agent, (ampacent), 3% by weight. The mixture was extruded to form a colorant mixture. The extruded triclosan/colorant/mold-release agent mixture was then compounded with a high density polyethylene (HDPE) polymer to form the resin to be used in manufacturing containment compartments.

The resultant polymer resin was then injection molded to form two-component containment compartments for use as suture trays. As disclosed herein, one component is a channel cover member and the second, a base member. The construction and geometry of the suture holding trays are as shown in FIG. 1 and similar to those described U.S. Pat. Nos. 6,047,815; 6,135,272; and 6,915,623. The trays prepared as described above weighed 3 grams each and contained approximately 11.2 mg of triclosan. The channel cover members and the base members of each tray were joined through ultrasonic bonding.

Example 2

The suture package was assembled in the following manner: A 27" length of Vicryl® suture, size 1 and dyed (a braided multifilament suture composed of a copolymer made from 90% glycolide and 10% L-lactide, that is commercially available from Ethicon, Inc.), initially substantially free of an antimicrobial agent, was placed in the base member of the suture tray and covered with the channel cover member. The suture tray assemblies, each having the suture and the two-component suture tray comprised of HDPE and triclosan, were arranged in separate cavities created in peelable foil packaging material, i.e., ethyl acrylic acid-coated aluminum foil composite, having a Tyvek® gas-permeable vent mounted to an open end of the packaging material to allow the passage of air, water vapor and ethylene oxide into the interior of the cavities within the packaging material. The suture assemblies were then ethylene oxide sterilized, which conveniently subjected the suture assemblies to time, temperature and pressure conditions sufficient to vapor transfer an effective amount of the antimicrobial agent from the antimicrobial agent source, i.e., the suture tray incorporating triclosan, to the suture.

Example 3

After the sterilization process was complete, the individual cavities were sealed and the gas permeable vent was effectively excluded to form sealed packages each having a suture assembly contained therein.

The sterilized Vicryl® sutures of Example 2 were then subjected to a paired study, that is, the same suture samples were used for both the stability studies, measuring the concentration of triclosan (ppm) in the suture over time, and the zone of inhibition testing (ZOI). In addition, a Vicryl® suture of Example 2 was subjected to a uniformity study to ascertain whether or not triclosan was distributed evenly throughout the length of suture.

Example 3A

Parts Per Million Stability Testing

The suture samples from Example 2 were divided into two groups and placed in chambers for long term stability studies testing, run at both 25 and 50 deg. C. The study measured the amount of triclosan present in the suture in parts per million, compiling the data over a two-year period. The triclosan had vapor transferred from the suture holding tray to the suture during the sterilization process. The data from this study is in Table 1.

Example 3B

Zone of Inhibition Testing

The data included in the table below was from zone of inhibition testing performed on the sutures, when challenged with *Escherichia coli* ATCC 8739 grown in Tryptic Soy broth at 37° C. for 24 h. The culture was diluted in sterile 0.85% saline to create inocula with concentrations of approximately 1,000,000 cfu (colony forming units) per milliliter. For the test, the sutures that had been subjected to the stability test described in Example 3A were aseptically cut into 5-cm pieces. The pieces were placed in separate sterile Petri dishes with 0.1 ml of inoculum. Tryptic Soy agar was poured into the plates, and the plates were incubated at 37° C. for 48 h. Zones of inhibition were read as the distance in millimeters from the suture to the edge of visible growth. See Table 1.

TABLE 1

Paired Studies of Size 1 Dyed Vicryl ® Suture

| Time (days) | 11.2 mg (4 wt %) Triclosan ZOI (mm) | 11.2 mg (4 wt %) Triclosan ppm | Temp Degrees C. |
|---|---|---|---|
| 0 | 8.7 | 1322 | 25 |
| 30 | 11.1 | 1313 | 25 |
| 90 | 9.7 | 1212 | 25 |
| 150 | 10.3 | 1276 | 25 |
| 270 | 8.2 | 1344 | 25 |
| 360 | 9.5 | 1218 | 25 |
| 940 | 9.7 | 1395 | 25 |
| 0 | 8.7 | 1322 | 50 |
| 30 | 9.0 | 1389 | 50 |
| 90 | 10.6 | 1484 | 50 |
| 150 | 10.2 | 1346 | 50 |
| 360 | 7.4 | 1291 | 50 |
| 940 | 9.7 | 1476 | 50 |

Trays manufactured with 11.2 mg triclosan produced a suture presenting a zone of inhibition of 8.7 mm against *E. coli* at the start of the study. The suture contained 1322 ppm of triclosan at the start of the study and 1476 ppm after 940 days. Results of the tests described herein show that the use of an antimicrobial agent integrally included in the polymer forming the suture holding tray is an effective means of generating a product that exhibits a zone of inhibition when challenged with *E. coli*.

Example 3C

Triclosan Distribution Uniformity Study

Figure 2:
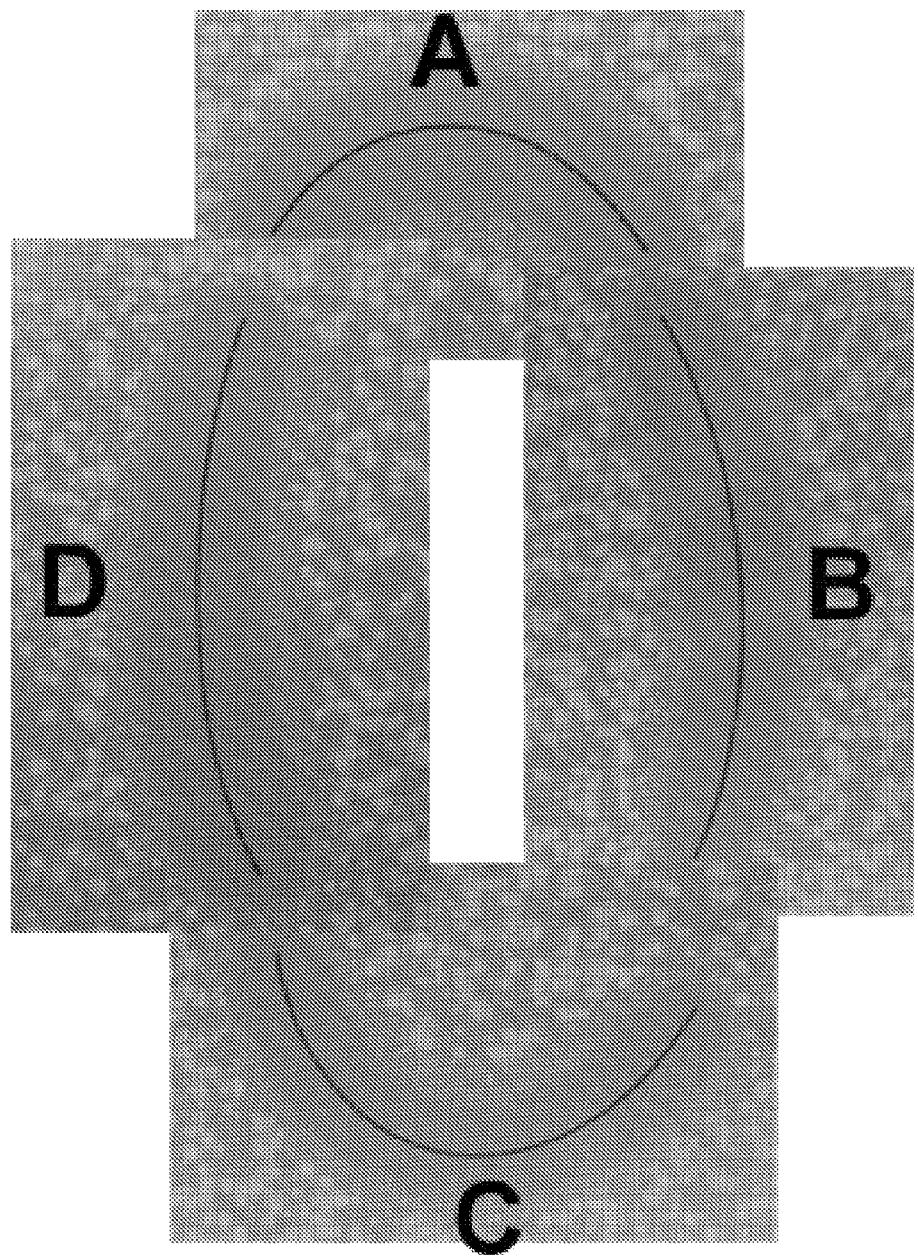
FIG. 2 is a photographic representation showing the uniformity of distribution by zone of inhibition method from containment compartment to after the sterilization process.
Figure 3:
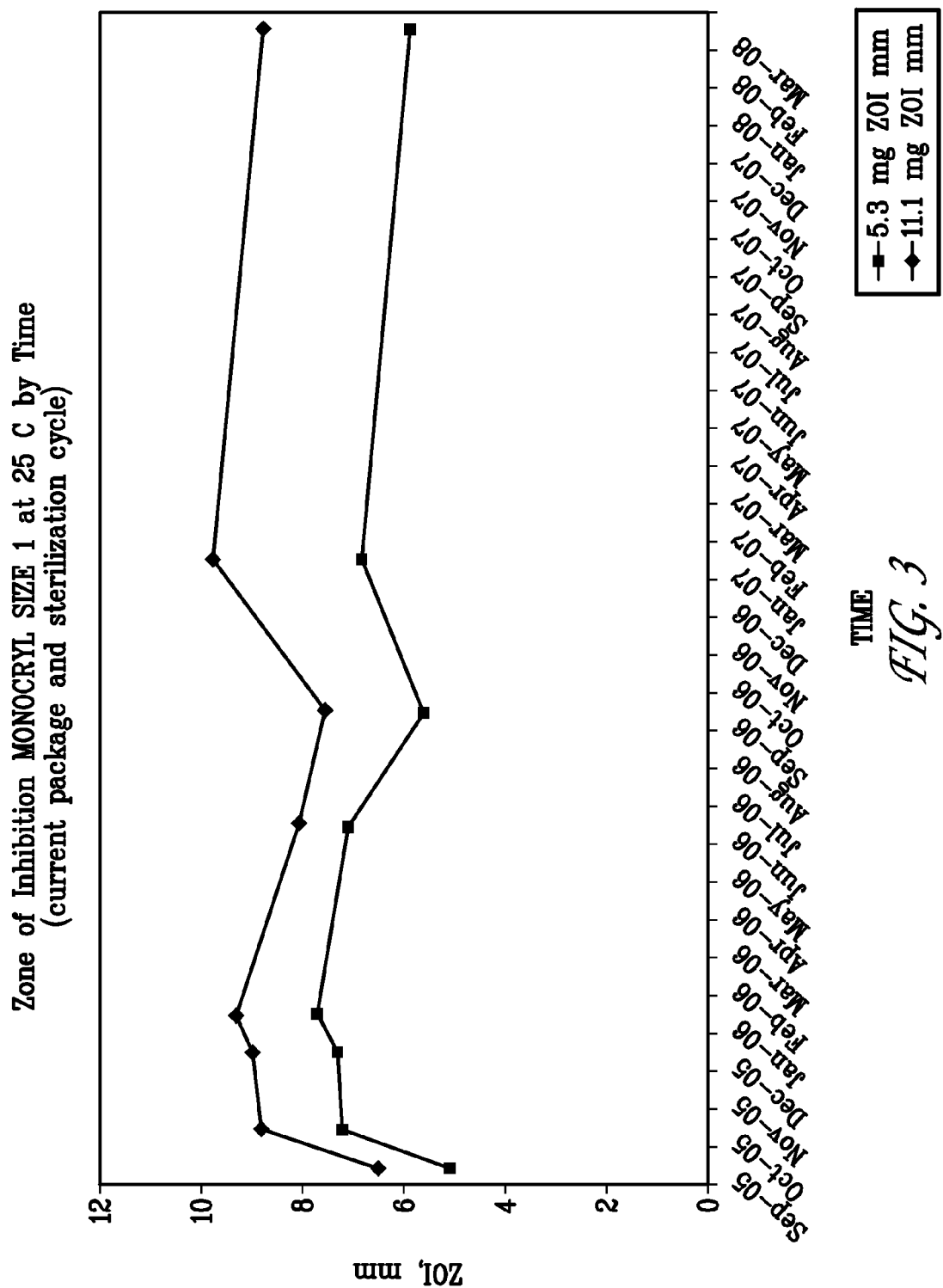
FIG. 3 presents zone of inhibition data versus time for a suture packaged in accordance herewith.
Figure 4:
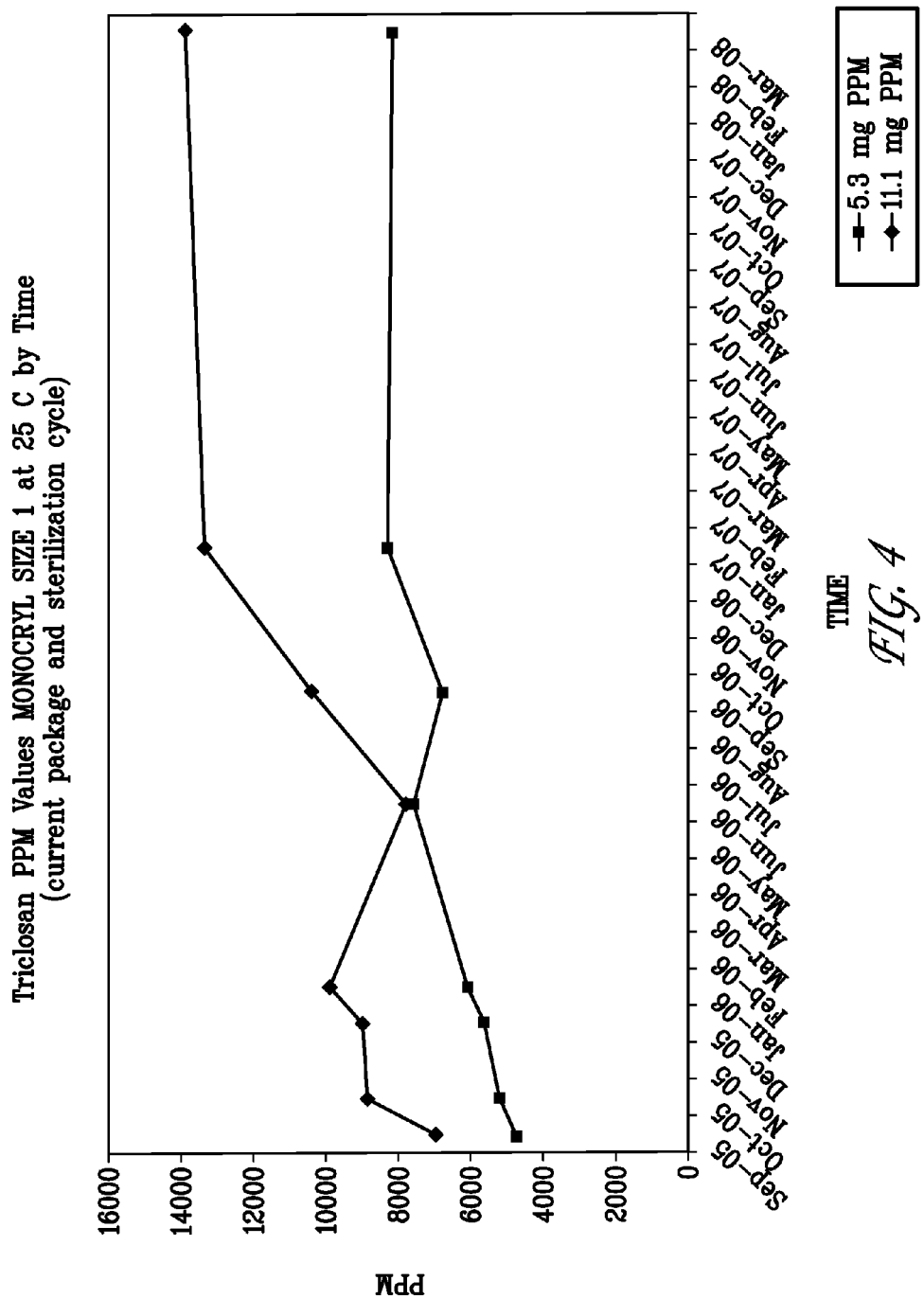
FIG. 4 presents parts-per-million triclosan values versus time for a suture packaged in accordance herewith.
Figure 5:
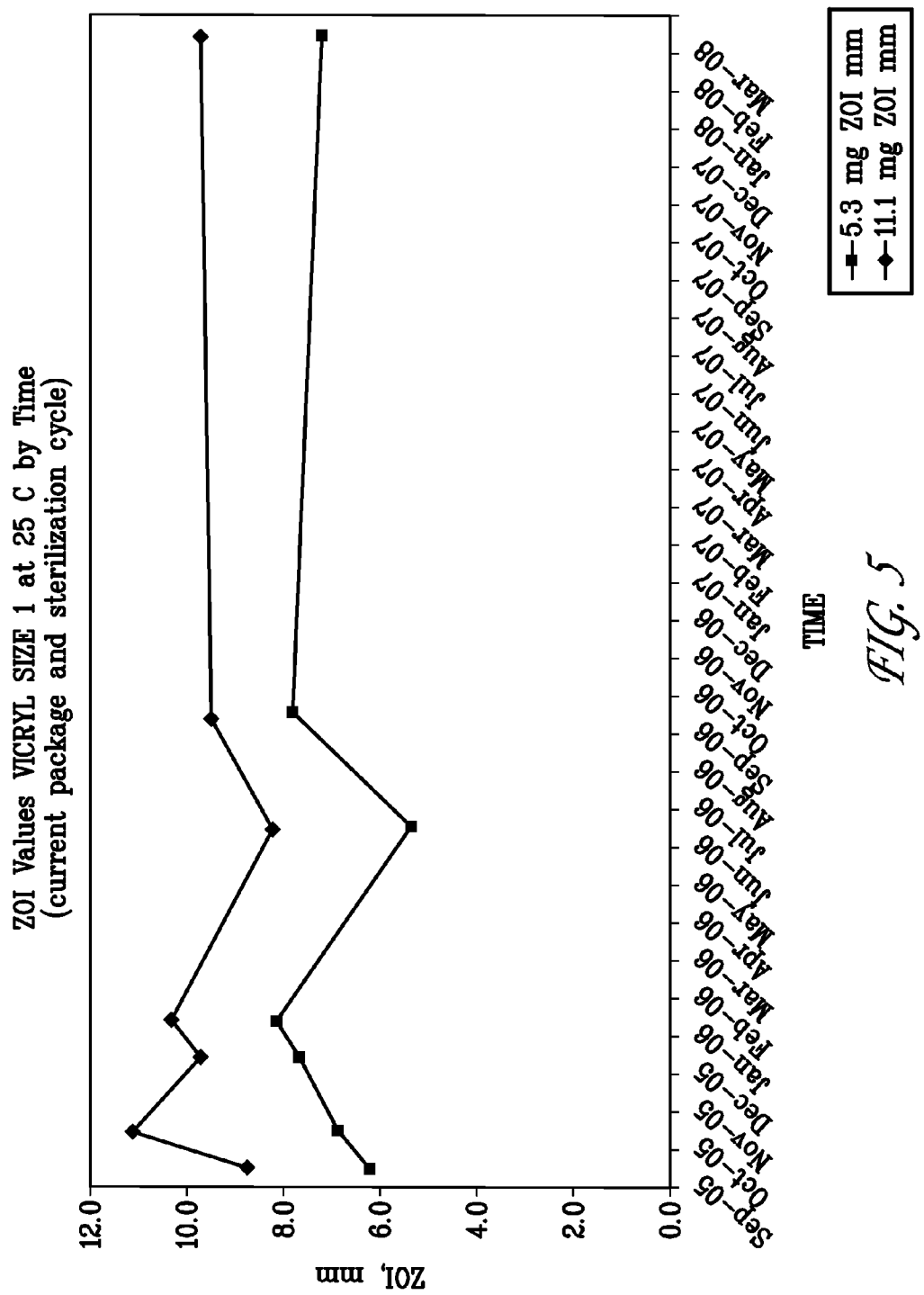
FIG. 5 presents zone of inhibition data versus time for a suture packaged in accordance herewith.
Figure 6:
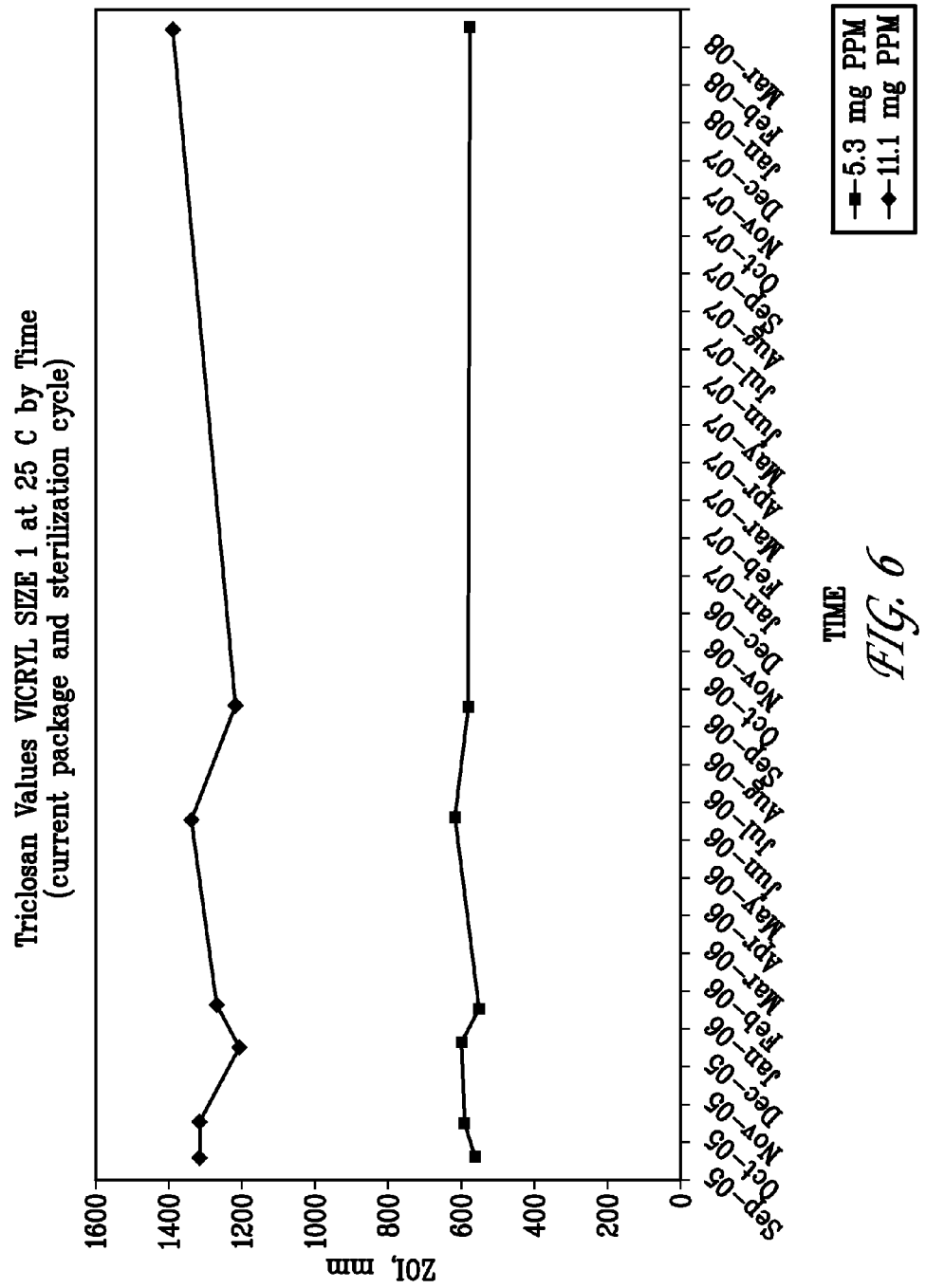
FIG. 6 presents parts-per-million triclosan values versus time for a suture packaged in accordance herewith.

The purpose of this study is to determine whether or not the triclosan is evenly distributed in and on the suture, that is, whether or not the triclosan that had vapor transferred from the suture tray to the suture has transferred uniformly to the sutures regardless of the position of the suture in the tray. FIG. 2 illustrates an empty suture package from Example 2 used in this study. The sides a, b, c, and d are identified in FIG. 2 and correspond to sides a, b, c, and of FIG. 1.

One package of the Vicryl® suture of Example 2 was opened to reveal the sutures within. A suture length which included one full circumference of the tray was cut from the whole. The piece was further cut into four strips, one from each of the four quadrants of the package, a, b, c, and d. A zone of inhibition test was conducted on these samples. FIG. 2 shows the size of the zone of inhibition for each side, proving that the position of the suture in the package does not significantly affect the size of the zone of inhibition. Therefore, the triclosan was deposited uniformly throughout the package.

In an identical manner, trials were run on sutures constructed of seven materials—Coated Vicryl® (polyglactin 910), PDS-II (polydioxanone), Monocryl® Plus (poliglecaprone 25), Ethilon® Nylon, Ethibond Excel® Polyester, Prolene® Polypropylene, and silk, testing 3 sizes of each suture—1, 2/0, and 6/0. The amount of triclosan added to the HDPE polymer included the values in the range from 2 to 9, specifically: 2, 4, 6, and 9% by weight of HDPE. The weight percents of triclosan amounted to 5.3, 11.2, 17.1, and 27.1 mg of triclosan per 3 gm tray respectively, as shown in Table 2.

TABLE 2

Paired Studies of Size 1 Dyed Vicryl ® Suture

| Time Days | 5.3 mg ZOI mm | 11.2 mg ZOI mm | 17.1 mg ZOI mm | V27.1 mg ZOI mm | 5.3 mg ZOI PPM | 11.2 mg ZOI PPM | 17.1 mg ZOI PPM | 27.1 mg ZOI PPM | Temp. C |
|---|---|---|---|---|---|---|---|---|---|
| 0 | 6.2 | 8.7 | 10.9 | 9.6 | 566 | 1322 | 2414 | 3869 | 25 |
| 30 | 6.9 | 11.1 | 17.4 | 18.2 | 586 | 1313 | 2303 | 3922 | 25 |
| 90 | 7.6 | 9.7 | 14.8 | 18.8 | 600 | 1212 | 2285 | 3863 | 25 |
| 150 | 8.1 | 10.3 | 11.5 | 15.6 | 551 | 1276 | 2558 | 4092 | 25 |
| 270 | 5.3 | 8.2 | | | 622 | 1344 | | | 25 |
| 360 | 7.8 | 9.5 | | | 583 | 1218 | | | 25 |
| 940 | 7.2 | 9.7 | 13.0 | 19.0 | 579 | 1395 | 2464 | 3975 | 25 |
| 0 | 6.2 | 8.7 | 10.9 | 9.6 | 566 | 1322 | 2414 | 3869 | 50 |
| 30 | 7.2 | 9.2 | 12.3 | 21.3 | 639 | 1389 | 2523 | 3448 | 50 |
| 90 | 7.7 | 10.6 | 14.2 | 41.0 | 645 | 1484 | 2403 | 3861 | 50 |
| 150 | 8.1 | 10.2 | 13.4 | 41.0 | 623 | 1346 | 2515 | 3659 | 50 |
| 360 | 6.6 | 7.4 | | | 674 | 1291 | | | 50 |
| 940 | 7.4 | 9.7 | 13.0 | 19.0 | 769 | 1476 | 2414 | 2996 | 50 |

Trays manufactured with 5.3 mg triclosan produced sutures that presented a 6.2 mm zone of inhibition at time zero. The suture at time zero had 566 ppm of triclosan present. It is clear from the data that as the triclosan levels increase in the tray, the zone of inhibition and the amount of triclosan present also increase. The level of the zone of inhibition and the levels of triclosan (ppm) are also affected by storage conditions. Based on the above data it is possible to achieve a ZOI of suitable length and effective levels of triclosan by selecting suitable parameters.

Example 4

Effect of Time on Efficacy

Suture packages were produced in accordance with Example 2. Additional suture packages were also produced in accordance with Example 2, with the exception that Size 1 Monocryl® Plus sutures were substituted for the Vicryl® sutures. Periodically, over a 30-month period, the zones of inhibition was tested for each packaged product type. Additionally, parts per million triclosan values were recorded for each packaged product type. These data are presented in FIGS. 3-6 and depict triclosan transfer as a function of time.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

What is claimed:

1. A packaged antimicrobial suture comprising:
   a containment compartment molded from a polymeric resin comprising a polymeric material and an antimicrobial agent;
   a suture comprising one or more surfaces and positioned within said containment compartment; and
   an outer package cover having an inner surface for covering said containment compartment having said suture therein,
   wherein said outer package cover, said containment compartment and said suture are subjected to time, temperature and pressure conditions sufficient to vapor transfer an effective amount of said antimicrobial agent from said containment compartment to said suture and said inner surface of said outer package cover, while retaining an effective amount of said antimicrobial agent on said containment compartment, thereby substantially inhibiting bacterial colonization on said suture and said containment compartment.

2. The packaged antimicrobial suture of claim 1, wherein said suture positioned within said containment compartment is substantially free of antimicrobial agent.

3. The packaged antimicrobial suture of claim 1, wherein said suture positioned within said containment compartment is coated with antimicrobial agent.

4. The packaged antimicrobial suture of claim 1, wherein said antimicrobial agent is selected from said group consisting of halogenated hydroxyl ethers, acyloxydiphenyl ethers, and combinations thereof.

5. A packaged medical device comprising:
   a containment compartment molded from a polymeric resin comprising a polymeric material and an antimicrobial agent;
   a medical device comprising one or more surfaces and positioned within said containment compartment; and
   an outer package cover having an inner surface for covering said containment compartment having said medical device therein,
   wherein said outer package cover, said containment compartment and said medical device are subjected to time, temperature and pressure conditions sufficient to vapor transfer an effective amount of said antimicrobial agent from said containment compartment to said medical device and said inner surface of said outer package cover, while retaining an effective amount of said antimicrobial agent on said containment compartment, thereby substantially inhibiting bacterial colonization on said medical device and said containment compartment.

6. A packaged antimicrobial suture comprising:
   a containment compartment molded from a polymeric resin comprising a polyolefin and an antimicrobial agent selected from the group consisting of halogenated hydroxyl ethers, acyloxydiphenyl ethers, and combinations thereof;
   a suture comprising one or more surfaces and positioned within said containment compartment; and
   an outer package cover having an inner surface for covering said containment compartment having said suture therein,
   wherein said outer package cover, said containment compartment and said suture are subjected to time, temperature and pressure conditions sufficient to vapor transfer an effective amount of said antimicrobial agent from said containment compartment to said suture and said inner surface of said outer package cover, while retaining an effective amount of said antimicrobial agent on said containment compartment, thereby substantially inhibiting bacterial colonization on said suture and said containment compartment.

7. The packaged antimicrobial suture of claim 6, wherein the polyolefin is high density polyethylene and the antimicrobial agent is triclosan.

* * * * *